United States Patent [19]
Zeeck et al.

[11] Patent Number: 5,189,150
[45] Date of Patent: Feb. 23, 1993

[54] OASOMYCINS

[75] Inventors: Axel Zeeck, Göttingen; Siegrid Philipps, Celle; Susanne Grabley, Königstein; Ernold Granzer, Kelkheim/Taunus; Klaus Hütter, Bad Soden am Taunus; Ralf Thiericke, Dietzenbach; Joachim Wink, Rödermark, all of Fed. Rep. of Germany

[73] Assignee: Hoechst Aktiengesellschaft, Frankfurt, Fed. Rep. of Germany

[21] Appl. No.: 781,928

[22] Filed: Oct. 24, 1991

[30] Foreign Application Priority Data

Oct. 26, 1990 [DE] Fed. Rep. of Germany ....... 4034110
Nov. 15, 1990 [DE] Fed. Rep. of Germany ....... 4036360

[51] Int. Cl.$^5$ .................. C07H 17/08; C07D 313/00
[52] U.S. Cl. ..................... 536/6.5; 549/266; 435/76; 435/117; 435/822; 435/886
[58] Field of Search ................ 536/6.5; 514/31, 450; 549/206; 435/886, 76, 822, 117

[56] References Cited

U.S. PATENT DOCUMENTS

| | | | |
|---|---|---|---|
| 2,943,023 | 6/1960 | Ninet | 435/76 |
| 2,990,330 | 6/1961 | Galtani | 435/76 |
| 4,397,950 | 8/1983 | Dolak et al. | 435/125 |
| 4,415,669 | 11/1983 | Hernandez | 435/253 |
| 4,454,228 | 6/1984 | Whaley et al. | 435/253 |

FOREIGN PATENT DOCUMENTS

| | | |
|---|---|---|
| 0357226A1 | 3/1990 | European Pat. Off. |
| 0431874A1 | 6/1991 | European Pat. Off. |
| 2053214A | 2/1981 | United Kingdom |

OTHER PUBLICATIONS

J. Pawlak et al., "The Structure of Lienomycin, a Pentaene Macrolide Antitumor Antibiotic," The Journal of Antibiotics, 33: 998-1004 (1980).

*Primary Examiner*—Johnnie R. Brown
*Assistant Examiner*—Elli Peselev
*Attorney, Agent, or Firm*—Finnegan, Henderson, Farabow, Garrett and Dunner

[57] ABSTRACT

Novel macrolactones with pharmacological effects can be prepared with the aid of Streptoverticillium and Streptomycetes strains.

1 Claim, No Drawings

OASOMYCINS

Antiobiotics from Streptomycetes are active substances which have been known for a long time, are derived from microorganisms and can be used in a variety of ways. J.V. Uri (Acta Microbiologica 33, 271 (1986)) describes non-polygenic macrolide antibiotics from Streptomycetes, the desertomycins. These compounds have a broad anti-bacterial spectrum and selective antifungal activity. It has been found that Streptoverticillium and Streptomyces strains are able to produce novel macrocyclic lactones, the oasomycins. These compounds have pharmacological and thus therapeutic activity and can be employed, in particular, advantageously as antibacterial agent and as inhibitors of cholesterol biosynthesis with corresponding pharmacological benefit.

Hence the invention relates to:

1. A process for the preparation of the compound of the formula I

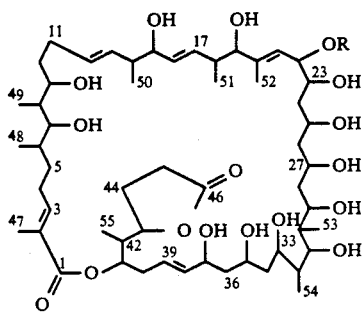

in which R is hydrogen or the group

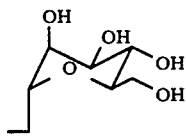

which comprises cultivating Streptoverticillium sp. and/or Streptomyces sp. in a nutrient medium until the compound of the formula I accumulates in the culture.

2. A use of the compound of the formula I as anti-bacterial agent or as inhibitor of cholesterol biosynthesis, and the pharmacological utilization thereof.

The invention is described in detail hereinafter, especially in its preferred embodiments. The invention is furthermore defined in the patent claims.

The compound according to the invention is preferably prepared using Streptoverticillium sp. DSM 5989 and Streptomyces sp. DSM 5990. Both strains were isolated from soil samples from India and deposited at the Deutsche Sammlung von Mikroorganismen (German Micro-organism Collection) in accordance with the rules of the Budapest Treaty on June 18, 1990, under the above-mentioned number.

The strain Streptoverticillium sp. DSM 5989 has red spores. The spore chains are verticillate and their surface is smooth. The strain Streptomyces sp. DSM 5990 has white spore chains which are arranged in narrow spirals. The surface of the spores appears smooth.

The compound of the formula I is produced by Streptoverticillium sp. and Streptomyces sp., preferably DSM 5989 and DSM 5990, in a nutrient solution which contains a carbon source and a nitrogen source and the customary inorganic salts. It is, of course, also possible to employ in place of the strains DSM 5989 or DSM 5990 the mutants and variants thereof as long as they synthesize this compound. Mutants of this type can be produced in a manner known per se by physical means, for example irradiation, such as with ultraviolet radiation or X-rays, or chemical mutagens such as, for example, ethyl methanesulfonate (EMS), 2-hydroxy-4-methoxy-benzophenone (MOB) or N-methyl-N'-nitro-N-nitrosoguanidine (MNNG).

Suitable and preferred carbon sources for the aerobic fermentation are assimilable carbohydrates and sugar alcohols, such as glucose, lactose or D-mannitol, and carbohydrate-containing natural products such as malt extract. Suitable nitrogen-containing nutrients are: amino acids, peptides and proteins and the degradation products thereof, such as peptones or tryptones, also meat extracts, milled seeds, for example of corn, wheat, beans, soybean or the cotton plant, distillation residues from the production of alcohol, meat meals or yeast extracts, but also ammonium salts and nitrates. Examples of inorganic salts which the nutrient solution can contain are chlorides, carbonates, sulfates or phosphates of the alkali metals or alkaline earth metals, iron, zinc, cobalt and manganese.

The production of the compound of the formula I takes place especially well in a nutrient solution which contains about 0.2 to 5%, preferably 1 to 4%, soybean meal and 0.2 to 5%, preferably 1 to 4%, mannitol, in each case based on the weight of the complete nutrient solution. Similarly good results are also obtained with a nutrient solution which contains 0.2 to 5%, preferably 1 to 3%, rolled oats and 0.1 to 10 ml, preferably 1 to 5 ml, of an aqueous trace element solution composed of 0.1 to 10% calcium chloride, 0.01 to 5% iron(III) citrate, 0.01 to 0.1% manganese sulfate, 0.001 to 0.5% zinc chloride, 0.0001 to 0.1% copper sulfate, 0.001 to 0.5% sodium tetraborate, 0.0001 to 0.01% cobalt chloride and 0.0001 to 0.01% sodium molybdate, and with a nutrient solution which contains about 0.2 to 10%, preferably 1 to 5%, glycerol, 0.01 to 1%, preferably 0.1 to 0.4%, casein peptone, 0.01 to 1%, preferably 0.05 to 0.5%, potassium hydrogen phosphate, 0.001 to 2%, preferably 0.01 to 0.8%, sodium chloride, 0.0001 to 0.5%, preferably 0.001 to 0.2%, magnesium sulfate and 0.1 to 20 ml, preferably 1 to 10 ml, of an aqueous trace element solution composed of 0.1 to 10% calcium chloride, 0.01 to 5% iron-(III) citrate, 0.01 to 0.1% manganese sulfate, 0.001 to 0.5% zinc chloride, 0.0001 to 0.1% copper sulfate, 0.001 to 0.5% sodium tetraborate, 0.0001 to 0.01% cobalt chloride and 0.0001 to 0.01% sodium molybdate, in each case based on the weight of the complete nutrient solution. The cultivation is carried out aerobically, that is to say, for example, submerged with shaking or stirring in shaking flasks or fermenters, where appropriate introducing air or oxygen. It can be carried out in a temperature range from about 18° to 35° C., preferably at about 25° to 35° C., in particular at 28° to 32° C. The pH range ought to be between 6 and 8, advantageously between 6.5 and 7.5. The microorganism is cultivated under these conditions in general for a period of 24 to 300 hours, preferably 36 to 140 hours.

The cultivation is advantageously carried out in several stages, i.e. initially one or more precultures are prepared in a liquid nutrient medium and are then transferred into the actual production medium, the main culture, for example in the ratio 1:10 by volume. The preculture is obtained, for example, by transferring a sporiolated mycelium into a nutrient solution and allowing it to grow for about 36 to 120 hours, preferably 48 to 72 hours. The sporiolated mycelium can be obtained, for example, by allowing the strain to grow for about 3 to 40 days, preferably 4 to 10 days, on a solid or liquid nutrient medium, for example yeast/malt agar or soybean meal/mannitol agar.

The progress of the fermentation can be monitored on the basis of the pH of the culture or of the mycelium volume and by chromatographic methods such as, for example, thin-layer chromatography or high pressure liquid chromatography, or testing the biological activity. The compound of the formula I is contained both in the mycelium and in the culture filtrate.

The said compound is isolated from the culture medium by known methods taking account of the chemical, physical and biological properties of the products. The antibiotic concentration in the culture medium or in the individual isolation stages can be tested using thin-layer chromatography, for example on silica gel with butanol/glacial acetic acid/water or ethyl acetate/methanol/water mixtures as mobile phase. The detection in the case of fractionation by thin-layer chromatography can be effected, for example by staining reagents such as anisaldehyde or by biological testing, for example with bacteria, fungi or protozoa, expediently comparing the amount of produced substance with a calibration solution.

To isolate the compound I, culture broth and mycelium are initially extracted with non-polar organic solvents such as, for example, n-hexane, petroleum ether or halogenated hydrocarbons such as, for example, chloroform etc. in order to remove the non-polar impurities. Extraction is subsequently carried out with a polar organic solvent, for example lower alcohols, acetone and/or ethyl acetate, and mixtures of these solvents.

The pure compound of the formula I is isolated on suitable materials preferably, for example, on silica gel, alumina, ion exchangers or adsorber resins, by subsequent elution with organic polar solvents or solvent mixtures, such as, for example, alkyl acetates, mixtures of alkyl acetate with a lower alkanol, chloroform or methylene chloride, or mixtures of these solvents with lower alkanols, where appropriate also with water, or with a pH or salt gradient suitable for ion exchanger resins, such as, for example, sodium chloride or tris(hydroxymethyl)-aminomethane HCl (tris buffer), and combining the fractions with antibiotic activity.

The compound of the formula I is stable in the solid state and in solutions in the pH range between 1 and 8, in particular 3 and 7, and can thus be incorporated in conventional pharmaceutical formulations.

The compound according to the invention can be used as antibacterial agent as well as lipid regulator. The compound of the formula I in which R is hydrogen can, in particular, be used advantageously as lipid regulator, especially for inhibiting cholesterol biosynthesis.

The compound of the formula I can be used for the prophylaxis and treatment of diseases which are based on an elevated cholesterol level, especially coronary heart diseases, arteriosclerosis and similar diseases. The invention also relates to pharmaceutical formulations of the compound of the formula I.

Besides the active substance, it is also possible to use pharmaceutically acceptable additives such as diluents and/or excipient materials in the preparation of pharmaceuticals. By this are meant physiologically acceptable substances which convert the active substance into a form suitable for administration after mixing therewith.

Examples of suitable solid or liquid pharmaceutical preparations are tablets, coated tablets, powders, capsules, suppositories, syrups, emulsions, suspensions, drops or injectable solutions and products with protracted release of active substance. Examples of frequently used excipients and diluents which may be mentioned are various sugars or types of starch, cellulose derivatives, magnesium carbonate, gelatin, animal and vegetable oils, polyethylene glycols, water or other suitable solvents, and water-containing buffers, which can be made isotonic by adding glucose or salts.

It is also possible to use where appropriate surface-active agents, colorants and flavorings, stabilizers, and preservatives as further additives in the pharmaceutical formulations according to the invention. It is also possible to use pharmacologically acceptable polymeric excipients such as, for example, polyphenylpyrrolidones, or other pharmaceutically acceptable additives such as, for example, cyclodextrin or polysaccharides. The compounds can, in particular, also be combined with additives which bind bile acids, in particular non-toxic, basic anion exchangers which are not absorbable in the gastrointestinal tract.

The products can be administered orally, rectally or parenterally. It is possible and preferable to prepare the products in dosage units; tablets, capsules, suppositories are particular examples of suitable dosage units. Each dosage unit, in particular for oral administration, can contain up to 1000 mg, but preferably 10 to 100 mg, of the active ingredient. However, it is also possible to use dosage units above or below this, which are to be divided or multiplied where appropriate before administration.

It is possible where appropriate for the dosage units for oral administration to be microencapsulated in order to delay release or extend it over a longer period, such as, for example, by coating or embedding the active substance in particulate form in suitable polymers, waxes or the like.

Parenteral administration is possible using liquid dosage forms such as sterile solutions and suspensions which are intended for intramuscular or subcutaneous injection. Dosage forms of these types are prepared by dissolving or suspending an appropriate amount of active substance in a suitable physiologically acceptable diluent such as, for example, an aqueous or oily medium and sterilizing the solution or the suspension, where appropriate also using suitable stabilizers, emulsifiers and/or preservatives and/or antioxidants.

The oral administration form is preferred, especially from the viewpoint of a long duration of therapy, and represents a considerable facilitation of the prevention and therapy of the diseases mentioned above.

The pharmaceutical products are prepared by generally customary processes. The dosage regimen may depend on the type, age, weight and sex and medical condition of the patient or person at risk.

The invention is described in further detail in the examples which follow. Percentage data relate to weight unless otherwise indicated.

EXAMPLES 1. a) Preparation of a suspension of spores of the producer strain:

100 ml of nutrient solution [12.5 g of glycerol, 1 g of arginine, 1 g of NaCl, 1 g of dipotassium hydrogen phosphate, 0.5 g of magnesium sulfate, 2.5 ml of trace element solution A (3 g of calcium chloride, 1 g of iron(III) citrate, 0.2 g of manganese sulfate, 0.1 g of zinc chloride, 0.025 g of copper sulfate, 0.02 g of sodium tetraborate, 0.004 g of cobalt chloride, 0.01 g of sodium molybdate in 1 l of distilled water) add water to 1l; pH before sterilization 7.3] in a 500 ml sterile Erlenmeyer flask, are inoculated with the strain DSM 5989 or DSM 5990 and incubated at 28° C. and 150 rpm on a rotary shaker for 72 hours. Subsequently 20 ml of culture liquid are uniformly distributed in a sterile 500 ml Erlenmeyer flask containing the nutrient medium of the above-mentioned composition, to which 20 g of agar/1 has also been added to solidify, and decanted. These cultures are incubated at 30° C. for 10 to 14 days. The spores which have been produced after this time in one flask are rinsed out with 500 ml of deionized water which contains one drop of commercially available non-ionic surfactant (for example Triton X 100 supplied by Serva), immediately used further or stored at −22° C. in 50% glycerol.

b) Preparation of a culture or of a preculture of the producer strain in an Erlenmeyer flask:

A sterile 500 ml Erlenmeyer flask containing 100 ml of the nutrient solution described under a) is inoculated with a culture grown on a slant tube or with 0.2 ml of spore suspension and is incubated on a shaker at 150 rpm and 30° C. The maximum production of the compound of the formula I is reached after about 72 hours. A 48-hour old submerged culture from the same nutrient solution suffices for the inoculation of 10 and 100 l fermenters (inoculum about 5%).

2. Preparation of the compound of the formula I:

A 10 l fermenter is operated under the following conditions:

| | |
|---|---|
| Nutrient medium: | 20 g/l soybean meal |
| | 20 g/l mannitol |
| | pH 7.5 (before sterilization) |
| Incubation time: | 72 hours |
| Incubation temperature: | 30° C. |
| Stirrer speed: | 250 rpm |
| Aeration: | 4 l of air/min |

Foaming can be suppressed by repeated addition of a few drops of ethanolic polyol solution. The production maximum is reached after about 72 hours. The yields are about 100 mg/l.

3. Isolation of the compound of the formula I:

After completion of the fermentation of DSM 5989 or DSM 5990, the culture broth is filtered with the addition of about 2% of filtration said (for example Celite). The working up can be as shown in the following diagrams:

Working up/isolation
Diagram 1: Culture supernatant

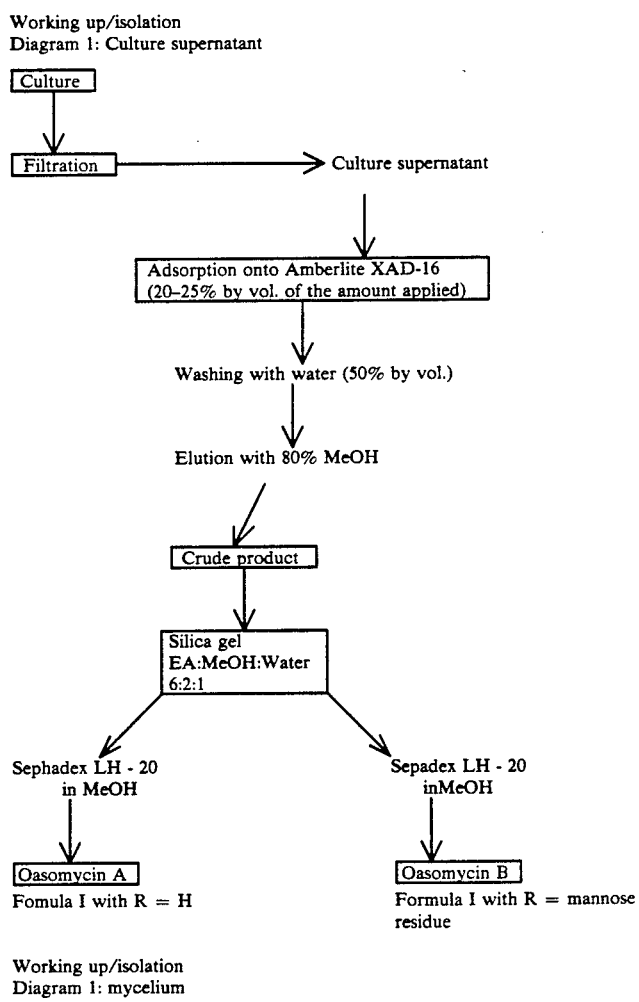

Working up/isolation
Diagram 1: mycelium

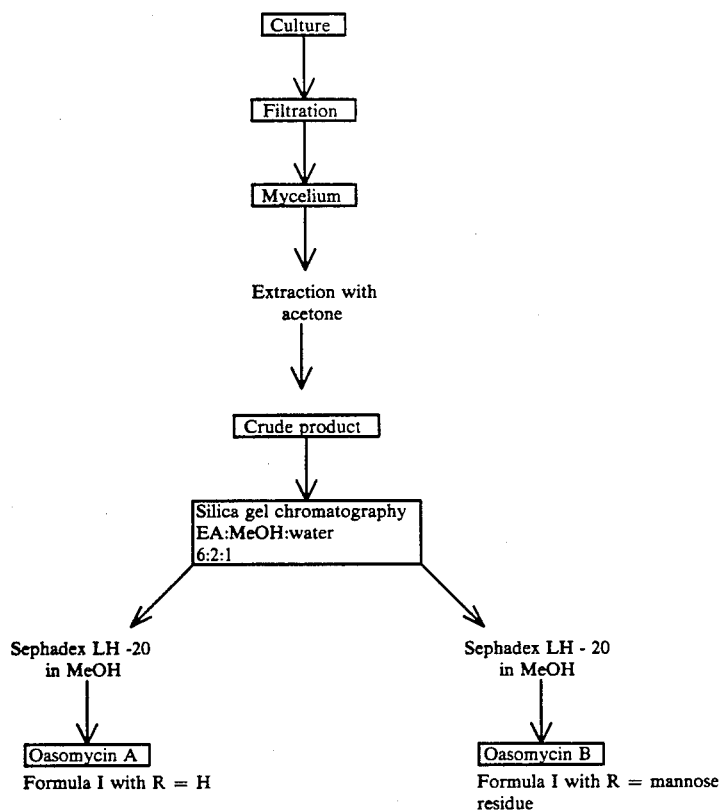

4. Biological tests on inhibition of cholesterol biosynthesis:

a) In vitro determination

Monolayers of HEP-G2 cells in lipoprotein-free nutrient medium are preincubated with appropriate concentrations of the substances to be tested, of the formula I, for 1 hour. The $^{14}C$-labeled biosynthesis precursor sodium [$^{14}C$] acetate is added and then incubation is continued for 3 hours. Subsequently, after addition of an internal standard of $^3H$-cholesterol, a portion of the cells is subjected to alkaline hydrolysis. The lipids from the hydrolyzed cells are extracted with a chloroform/methanol mixture. This lipid mixture is, after addition of carrier cholesterol, fractionated by preparative thin-layer chromatography and, after staining, the cholesterol band is isolated, and the amount of $^{14}C$-cholesterol formed from the $^{14}C$-precursor is determined by scintigraphy. Cellular protein was determined in an aliquot of the cells so that it is possible to calculate the amount of $^{14}C$-cholesterol formed from $^{14}C$-precursor per mg of cellular protein per unit time. The control is used for comparison of the inhibitory effect of an added test product, so that it is possible directly to state the inhibition of cholesterol biosynthesis at a particular molar concentration of the test product in the medium. The integrity of the cell culture and the absence of cell damage due to exposure to the product is assessed morphologically (light microscopy) and measured biochemically by determining the lactic dehydrogenase secretion into the incubation medium in aliquots of the cell culture. Lovastatin was used as standard product. The inhibition of cholesterol biosynthesis by the compound of the formula I with R=H is 72% at a concentration of $10^{-7}$ mol/l
41% at a concentration of $10^{-8}$ mol/l.

The inhibition of cholesterol biosynthesis by Lovastatin is 74% at $10^{-7}$ mol/l and 48% at $10^{-8}$ mol/l.

b) In vivo determination

Inhibition of hepatic cholesterol biosynthesis has effects on the reduction in serum lipids, as can be demonstrated in a chronic experiment on the male rat. Groups of male rats of the strain HOE: WISKf (SPF 71) with an initial weight of about 240 g receive the test products in polyethylene glycol 400 by gavage each day in the morning, the particular control group receiving only the vehicle. 24 hours after the last administration and after withdrawal of feed for 24 hours, blood was taken and the lipoproteins in the serum obtained from the pool of one rat group were separated using the preparative ultracentrifuge technique. The following density limits were used for separating VLDL, LDL and HDL in this case:

VLDL 1.006
LDL 1.04
HDL 1.21

Completely enzymatic methods from Boehringer/Mannheim were used to determine the cholesterol and the triglycerides, and the method of Lowry et al. was used for determination of protein.

The values measured for the compound of the formula I in which R is hydrogen are listed hereinafter, comparing with clofibrate:

| Compound | Dose mg/kg | Biological data | | | | | | |
|---|---|---|---|---|---|---|---|---|
| | | Total cholesterol | | | Glyc | Cholesterol | | |
| | | VDLD | LDL | HDL | VLDL | LDL | VLDL | HDL/LDL |
| Formula 1 | | | | | | | | |
| R = H | 20 | −30 | −45 | −4 | +2 | −32 | −6 | 1.74 |
| Clofibrate | 100 | −54 | −32 | −28 | −8 | −9 | −10 | 1.05 |

5. a) Characterization of the compound I in which R is hydrogen:

Oasomycin A was isolated as amorphous solid.
Melting point: 146° C.
Optical rotation: −13.1° (c=0.122, methanol).

Thin-layer chromatography:

Silica gel 60, F254: chloroform/methanol (9:1, v:v): Rf 0.0.
n-Butanol/acetic acid/water (upper phase) (4:1:5, v:v:v): Rf 0.45.
Staining characteristics: Ehrlich's reagent: brown; vanillin/sulfuric acid: brown/violet.
FAB—MS: m/e=1065 (M+K); 1049 (M+Na);
Molecular mass: 1027.3 ($C_{55}H_{94}O_{17}$).
IR (KBr): 3420 (br), 2960, 2930, 1780, 1725, 1710, 1600, 1570 cm$^{-1}$.
UV (MeOH):=202 nm (=14000); 220 (6100) +HCl:=202(16400);220(5700) +NaOH:=225(7000).

1H-NMR (500 MHz, DMSO—$d_6$)δ=0.86 (53-$H_3$), 078(55≦$H_3$), 0.64(54-$H_3$), 0.64(49-$H_3$), 1.54(52-$H_3$), 1.77(47'$H_3$), 0.78(48-$H_3$), 0.86(50-$H_3$), 0.99(51-$H_3$), 1.88 and 2.16(44-$H_2$), 2.16(4-$H_2$), 2.44(45-$H_2$), 1.90 and 2.18(11-$H_2$), 1.20 and 1.50(10-$H_2$), 2.32(40-$H_2$), 1.26 and 1.54(5-$H_2$), 1.52(6-H), 2.18(18-H), 1.46(30-H), 2.14(42-H), 1.26(32-H), 1.42(24-$H_{29}$, 1.58((8-H), 2.08(14-H), 1.11 and 1.42(34-$H_2$), 1.52(28-$H_2$), 1.40(26-$H_2$), 1.34 (36-$H_2$), 3.90(25-H), 3.82(35-H), 3.90(27-H), 4.06(33-H), 4.14 (37-H), 3.68(31-H), 4.06(23-H), 3.66(9-H), 3.62(29-H), 5.00 (41-H), 3.74(22-H), 3.74(15-H), 3.25(7-H), 4l48(43-H), 3.50 (19-H), 5.348(39-H), 5.26(21-H), 5.40(12-H), 5.34(16-H), 5.39 (13-H), 5.39(17-H), 5.48(38-H), 6.69(3-H).

13C—NMR(125.7MHz, DMSO—$d_6$) δ=9.4(q, C-53), 9.6 (q, C-55), 10.5 (q, C-54), 11.1 (q, C-49), 11.5(q,C-52), 12.1(q,C-47), 12.2(q, C-48), 15.21 (q, C-50), 16.8 (q,C-51), 24.8 (t, C-44), 26.0 (t, C-4), 28.2 (t, C-45), 28.9 t,C-11), 32.0 (t, C-10), 32.4 (t, C-40), 32.9 (t, C-5), 34.3 (d, C-6), 39.2 (d, C-18), 39.5 (d, C-30), 39.9 (d, C-42), 40.1 (d, C-32), 40.4 (t, C-24), 41.4 (d, C-8), 42.2 (d, C-14), 42.2 (t, C-34), 42.2 (t, C-28), 45.6 (t, C-26), 45.7 (t, C-36)k, 63.7 (d, C-25), 63.8 (d, C-35), 66.7 (d, C-27), 66.8 (d, C-33), 66.8 (d, C-37), 70.8 (d, C-31), 70.9 (d, C-23), 72.0 (d, C-9), 72.8 (d, C-29), 73.0 (d, C-41), 74.3 (d, C-22), 74.3 (d, C-15), 74.6 (d, C-7), 80.4 (d, C43), 81.0 (d, C-19), 122.4 (d, C-39), 126.8 (s, C-2), 126.9 (d, C-w21), 129.5 (d, C-12), 130.9 (d, C-16), 132.5 (d, C-13), 132.7 (d, C-17), 138.1 (s, C-20), 138.2 (d, C-38), 142.5 (d, C-3), 166.4 (s, C-1), 176.7 (s, C-46).

Elemental analysis: Calculated: C 64.30 H 9.22 Found: C 64.20 H 9.22.

b) Characterization of the compound I in which R is a mannose residue:

Oasomycin B was isolated as amorphous solid.
Melting point: 157° C.
Optical rotation: −24.6° (c=0.199, methanol).

Thin-layer chromatography

Silica gel 60, F254: chloroform/methanol (9:1, v:v): Rf 0.0.
n-Butanol/acetic acid/water (upper phase) (4:12:5, v:v:v): Rf 0.30.
Staining characteristics: Ehrlich's reagent: brown; vanillin/sulfuric acide: blue/violet.
FAB—MS: m/e=1228 (M+K); 1212 (M—Na);
Molecular mass: 1189.5 ($C_{61}H_{104}O_{22}$).
IR (KBr): 3400 (br), 2960, 2930, 1770, 1725, 1710, 1580 cm$^{-1}$.
UV (MeOH):=202 nm (=23100); 220(10900) +HCl:=202(24600); 220(10100) +NaOH:=218(14000).

1H-NMR (500 MHz, DMSO—$d_6$)δ=9,90 (53-$H_3$), 0.82 (55-$H_3$), 0,68 (54-$H_3$), 0,68 (49-$H_3$), 1,63 (52-$H_3$), 1,80 (47-$H_3$), 0,82 (48-$H_3$), 9,90 (50-$H_3$), 1,02 (51-$H_3$), 1,94 und 2,18 (44-$H_2$), 2,18 (4-$H_2$), 2,53 (45$H_2$), 1,96 und 2,21 (11-$H_2$), 1,24 und 1,50 (10-$H_2$), 2,36 (40-$H_2$), 1,32 und 1,50 (5-$H_2$), 1,57 (6-H), 2,24 (18-H), 1,48 (30-H), 2,18 (42-H), 1,44 (32-H), 1,30 (24-$H_2$), 1,62 (8-H), 2,12 (14-H), 1,23 (34-$H_2$), 1,59 (28-$H_2$), 1,42 (26-$H_2$), 1,30 (36-$H_2$), 3,48 und 3,68 (6'-$H_2$), 3,86 (25-H), 3,82 (35-H), 3,92 (27-H), 4,10 (33-H), 4,15 (37-H, 3,44 (4'-H), 3,82 (23-H), 3,54 (2'-H), 3,78 (31-H), 3,56 (3'-H), 3,64 (9-H), 3,60 (29-H), 5,02 (41-H), 3,40 (5'-H), 4,16 (22-H), 3,70 (15-H), 3,26 (7-H), 4,42 (43-H), 3,54 (19-H), 4,68 (1'-H), 5,20 (21-H), 5,52 (39-H), 5,40 (12-H), 5,37 (16-H), 5,42 (13-H), 5,48 (17-H), 5,52 (38-H), 6,72 (3-H).

13C—NMR (125,7 MHz, DMSO—$d_6$) δ=9,4 (q, c-53), 9,6 (q, C-55), 10,4 (q, C-54), 11,2 (q, C-49), 11,7 (q, C-52), 12,1 (q, C-47), 12,2 (q, C-48), 15,2 (q, C-50), 16,6 (q, C-51), 24,8 (t, C-44), 26,1 (t, C-4), 28,2 (t, C-45), 28,9 (t, C-11), 32,1 (t, C-10), 32,4 (t,C-40), 32,9 (t, C-5), 34,3 (d, C-6), 39,4 (d, C-18), 39,4 (d, C-30), 39,9 (d, C-42), 40,4 (d, C-32), 40,8 (t, C-24), 41,4 (d, C-8), 42,2 (d, C-14), 42,2 (t, C-34), 42,3 (t, C-28), 45,6 (t, C-26), 45,7 (t, C-36), 61,2 (t, C6'), 63,4 (d, C-25), 63,8 (d, C-35), 66,7 (d, C-27), 66,8 (d, C-33), 66,8 (d, C-37), 67,2 (d, C-4'), 69,4 (d, C-23), 70,6 (d, C-2'), 70,7 (d, C-31), 70,9 (d, C-3'), 72,0 (d, C-9), 72,8 (d, C-29), 73,0 (d, C-41), 73,5 (d,C-5'), 73,7 (d, C-22), 74,4 (d, C-15), 74,6 (d, C-7), 80,4 (d, C-43), 80,7 (d, C-19), 95,9 (d, C-1'), 122,2 (d, C-21), 122,4 (d, C-39), 126,9 (s, C-2), 129,5 (d, C-12), 131,0 (d, C-16), 132,6 (d, C-13), 132,7 (d, C-17), 138,2 (d, C-38), 142,5 (d, C-3), 143,2 (s, C-20), 166,4 (s, C-1), 176,7 (s, C-46).

Elemental analysis: Calculated: C 61.89 H 8.81 Found: C 59,91 H 8.85

We claim:

1. The compound of the formula I

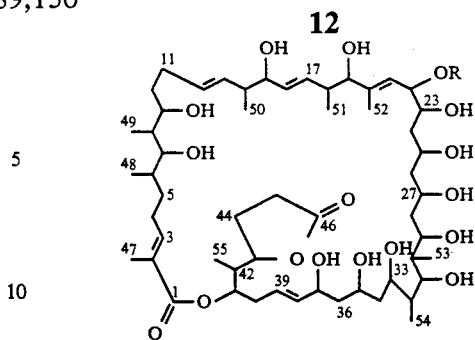
in which R is hydrogen or the group
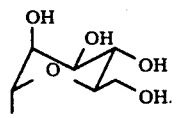
* * * * *